United States Patent [19]

Salinas, III et al.

[11] Patent Number: 5,202,511
[45] Date of Patent: Apr. 13, 1993

[54] CATALYST DILUENT FOR OXYCHLORINATION PROCESS

[75] Inventors: Leopoldo Salinas, III; Thomas E. Morris, both of Lake Jackson, Tex.; Arnold D. Harley, Midland, Mich.

[73] Assignee: The Dow Chemical Company, Midland, Mich.

[21] Appl. No.: 394,408

[22] Filed: Aug. 16, 1989

[51] Int. Cl.$^5$ .......................................... C07L 17/156
[52] U.S. Cl. .................................. 570/245; 570/243
[58] Field of Search .............................. 570/245, 243

[56] References Cited

U.S. PATENT DOCUMENTS

| | | |
|---|---|---|
| 3,184,515 | 5/1965 | Penner et al. |
| 3,240,827 | 3/1966 | Laine et al. |
| 3,454,663 | 7/1969 | Ryckaert et al. |
| 3,699,178 | 10/1972 | Suzuki et al. |
| 4,123,467 | 10/1978 | Campbell et al. |
| 4,206,180 | 6/1980 | Campbell et al. |
| 4,424,143 | 1/1984 | Shiozaki et al. |
| 4,788,357 | 11/1988 | Dummer et al. |
| 4,788,358 | 11/1988 | Riedl et al. |
| 4,788,759 | 11/1988 | Schuchardt. |

FOREIGN PATENT DOCUMENTS

| | | | |
|---|---|---|---|
| 0060317 | 9/1982 | European Pat. Off. | 570/245 |
| 2649533 | 5/1977 | Fed. Rep. of Germany | 570/245 |
| 41-7948 | 4/1966 | Japan | 570/245 |
| 48-42607 | 12/1973 | Japan. | |
| 806570 | 12/1958 | United Kingdom. | |
| 967936 | 8/1964 | United Kingdom. | |
| 1012220 | 12/1965 | United Kingdom | 570/245 |
| 1104666 | 2/1968 | United Kingdom | 570/245 |

*Primary Examiner*—Howard T. Mars

[57] ABSTRACT

Alumina is used as a support for the CuCl2 catalyst and as a diluent in the oxychlorination of ethylene. When a low surface area alumina, e.g. high purity alpha-alumina, is used as diluent for the reaction, reduced oxidation and less chlorinated by-products are achieved. Alternatively, the alumina used as the catalyst support, e.g. a gamma-alumina which has a high surface area and higher amounts of impurities, can be used as diluent if it is impregnated with an alkali metal ion, e.g K+ ion, which is usually employed as a salt.

2 Claims, No Drawings

CATALYST DILUENT FOR OXYCHLORINATION PROCESS

BACKGROUND OF THE INVENTION

Oxychlorination processes for chlorinating olefinic hydrocarbons are well known to the art. The olefin is fed together with oxygen or an oxygen-containing gas and hydrogen chloride over a copper chloride ($CuCl_2$) catalyst at an elevated temperature. The process can be conducted in either a fixed or fluid bed. The copper chloride is supported on an inert material, e.g. alumina. Frequently, in fixed beds the catalyst is provided in layers of varying concentrations and/or with alternating layers of unburdened catalyst support or other inert material. Diluents provide a means of controlling the highly exothermic reaction which, if not controlled, can cause "hot spots" and excessive oxidation losses of the olefin. Patents disclosing various means of conducting this process include Br. 806,570 which uses silicon carbide as diluent: Br. 967,936 which employs graphite as a diluent; U.S. Pat. No. 3,184,515 which also employs graphite, but mixed with the catalyst-bearing particles so that the diluent is present in a higher proportion at the inlet end and the catalyst-bearing particles are in higher proportion at the outlet end of the bed. U.S. Pat. No. 3,240,827 discloses the use of at least 50 volume percent of a macroporous carbon as diluent with the catalyst-bearing particles. The use of an alumina $\alpha$-monohydrate as a catalyst support is claimed to permit conducting the oxychlorination reaction at a lower temperature in U.S. Pat. No. 3,454,663. In U.S. Pat. No. 3,699,178 the temperature is controlled by varying the distribution of the catalyst particles so that the larger particles are near the inlet while the smaller are at the outlet of the reactor. In addition to the diluents above-indicated, silica and glass beads also have been disclosed as useful.

It is also known that the addition of KCl as a promoter with the $CuCl_2$ employed as a catalyst reduces oxidation losses and the formation of ethyl chloride. Representative of patents which employ potassium chloride as promoter for the catalyst are British Patent 967,936 and U.S. Pat. Nos. 4,123,467: 4,206,180 and 4,424,143.

SUMMARY OF THE INVENTION

Alumina is used as a support for the $CuCl_2$ catalyst in an oxychlorination reaction. A diluent is used to control the heat of reaction. A low surface area alumina, having low silica and $Na_2O$ impurities, when used as diluent provides reduced oxidation and chlorinated by-products. Alternatively, the alumina used as the catalyst support, e.g. a gamma-alumina which has a high surface area and higher amounts of impurities, can be used as diluent when it is impregnated with an alkali metal ion, e.g. $K^+$ ion, usually employed as a salt such as KCl, $K_2SO_4$ or the like.

DETAILED DESCRIPTION OF THE INVENTION

Temperatures, pressures, mole ratios and the like parameters for the oxychlorination are well known to the art. Thus, temperatures in the range of from about 200° to about 300° C., pressures of from about 15 to about 100 psig and mole ratios of from about 1.8 to about 2.2 moles of HCl and from about 0.4 to about 0.8 mole of oxygen per mole of ethylene.

The copper catalyst is impregnated onto a support as is known to the art, e.g. by soaking in an aqueous solution of $CuCl_2$ which also contains an alkali metal salt such as KCl. The amount of catalyst and promoter employed is sufficient to provide a finished catalyst containing from about 3 to about 5 percent by weight $Cu^{++}$ ion and from about 1 to 2 percent by weight of alkali metal ion on the catalyst support. The support used is preferably high surface area gamma-alumina, i.e. having a surface area of from about 100 to about 380 $m^2/g$. Other alkali metal salts such as NaCl, $Na_2SI_4$, $KNO_3$, $K_2SO_4$, $K_2C_2H_3O_2$, CsCl, $Cs_2CO_3$ and the like may be used to provide the alkali metal ion.

The preferred diluent is a low surface area, high purity alpha-alumina, having a surface area of from about 0.01 to about 10 $m^2/g$ and having no more than about 0.2 percent $SiO_2$ and about 0.1 percent $Fe_2O_3$ as impurities. Any other form of alumina may be employed, e.g. chi-alumina or boehmite, providing it has the required low surface area and high purity.

A more active alumina material, such as the high surface area gamma-alumina used as the catalyst support, is also satisfactory for use as a diluent providing it is impregnated with sufficient alkali metal ion to reduce to an acceptable level the formation of by-product aliphatic and olefinic chlorinated hydrocarbons, such as ethyl chloride, vinyl chloride and dichloroethylene.

A high surface area material, of course, will have more sites available for reaction to produce undesired chloro-hydrocarbon by-products. High surface area materials of high purity, of course, will require less of the alkali metal salt than those containing more impurities. With high surface area materials as diluent, the amount of alkali metal ion will vary from about 0.1 to about 10 percent by weight, depending on their purity. The high surface area aluminas normally available require at least about 1–2 percent, but preferably about 5 percent by weight based on the weight of the alumina. The latter amount places the efficacy of such aluminas in the same range as that of low surface area, high purity alumina which is the preferred diluent. The correct amount to use is that which is sufficient to counteract the effect of the impurities, such as iron and silicon compounds, which are believed to cause the by-product formation.

The following examples are illustrative of the invention. Comparative examples are also provided.

EXAMPLE 1

Oxychlorination of ethylene is performed in a Berty reactor, which consists of an autoclave containing a 3-inch diameter mesh basket filled with catalyst and a fan to stir the gases contacting the catalyst. The operating conditions for the experiments are a temperature of 240° C. and a pressure of 40 psig. The gas composition consists of a mole ratio of $HCl/O_2/C_2H_4$ of 2/0.375/1. The feed rate of ethylene is the same for all experiments except for the catalyst which is used without diluent: the HCl and $O_2$ ratios to $C_2H_4$ are maintained constant so that a conversion of ca.30% is provided as a basis for comparison of the different catalysts. A total yield is obtained by multiplying the conversion (C) times the selectivity (S) for a better comparison of the experiments. The catalyst consists of 3.6% $Cu^{++}$ and 1.8% $K^+$, both in the chloride form on high surface area gamma-alumina ($300 m^2/g$ BET surface area). This catalyst was employed in Experiments 1a–11, which are described as follows:

(1a) No diluent.
(1b) A diluent of the same high surface area gamma-alumina used as the support for the catalyst
(1c) The gamma-alumina diluent of (1b) containing 1.0% $K^+$ as $KCl$
(1d) The gamma-alumina diluent of (1b) containing 2.0% $K^+$ as $KCl$
(1e) The gamma-alumina diluent of (1b) containing 5.0% $K^+$ as KCl and
(1f) A diluent of high purity, low surface area alpha-alumina (0.5 $m^2$/g) with no potassium.

TABLE

Results are shown in the following Table.

| Ex. No. | Flow rate* gmol $C_2H_4$/hr | % HCL conversion | % selectivity to EDC | % $C_2H_4$ conv. to $C_2H_5Cl$ | $C \times V$ = total yield |
|---|---|---|---|---|---|
| 1a | 1.30 | 30.66 | 98.35 | 0.46 | 30.15 |
| 1b | 1.00 | 33.52 | 97.41 | 0.84 | 32.65 |
| 1c | 1.00 | 32.35 | 97.76 | 0.68 | 31.63 |
| 1d | 1.00 | 29.88 | 97.60 | 0.67 | 29.16 |
| 1e | 1.00 | 29.31 | 98.50 | 0.43 | 28.87 |
| 1f | 1.00 | 31.78 | 98.53 | 0.47 | 31.31 |

*It was necessary to increase the flow rate in Experiment 1a in order to maintain the conversion near the 30% level.

While the Experiment with no diluent (1a) gives only a small amount of ethyl chloride, running a catalyst with no diluent is impractical because of "hot spotting" which causes the amount of hydrocarbon lost of carbon oxides to be unacceptable. The high surface area diluent, when impregnated with an alkali metal ion, performs well with respect to minimizing the production of ethyl chloride providing sufficient alkali metal salt is employed. The low surface area diluent, however, is preferred because it produces less of the undesirable ethyl chloride without the use of the alkali metal salt.

We claim:

1. In the method of producing 1,2-dichloroethane by an oxychlorination process wherein ethylene is reacted with HCl and oxygen over a copper chloride catalyst promoted with an alkali metal salt on a high surface area support and wherein a diluent is employed, the improvement which comprises employing a low surface area diluent wherein the diluent is a chi-alumina.

2. In the method of producing 1,2-dichloroethane by an oxychlorination process wherein ethylene is reacted with HCl and oxygen over a copper chloride catalyst promoted with an alkali metal salt on a high surface area support and wherein a diluent is employed, the improvement which comprises employing a low surface area diluent wherein the diluent is boehmite.

* * * * *